United States Patent [19]
Klock, Jr.

[11] Patent Number: 6,048,707
[45] Date of Patent: Apr. 11, 2000

[54] FLUOROPHORE ASSISTED DERIVATIZATION ANALYSIS OF CARBOHYDRATES

[75] Inventor: John C. Klock, Jr., Mill Valley, Calif.

[73] Assignee: Glyko, Inc., Novato, Calif.

[21] Appl. No.: 07/938,832

[22] Filed: Aug. 31, 1992

Related U.S. Application Data

[63] Continuation-in-part of application No. 07/753,196, Aug. 30, 1991, abandoned.

[51] Int. Cl.$^7$ ..................................................... C12Q 1/34
[52] U.S. Cl. ............................................. 435/18; 536/127
[58] Field of Search .......................... 204/182.8; 536/54, 536/127, 123, 123.1; 378/62; 435/18; 436/94; 430/32; 250/310.08

[56] References Cited

U.S. PATENT DOCUMENTS

| | | | |
|---|---|---|---|
| 3,971,702 | 7/1976 | Maekawa | 195/63 |
| 4,852,137 | 7/1989 | Mackay | 378/62 |
| 4,874,492 | 10/1989 | Mackay | 204/182.8 |
| 4,918,009 | 4/1990 | Nilsson | 435/73 |
| 4,975,165 | 12/1990 | Brandley | 204/182.1 |
| 5,019,231 | 5/1991 | Brandley et al. | 204/182.1 |
| 5,035,786 | 7/1991 | Brandley et al. | 204/182.1 |

FOREIGN PATENT DOCUMENTS

| | | |
|---|---|---|
| 271 440 | 11/1987 | European Pat. Off. . |
| WO 91/05256 | 4/1991 | WIPO . |
| WO 91/12275 | 8/1991 | WIPO . |
| WO 91/12276 | 8/1991 | WIPO . |
| WO 91/12520 | 8/1991 | WIPO . |

OTHER PUBLICATIONS

Lindberg and Lonngren, *Methods in Enzymology vol. 50*, pp. 3–32, Academic Press (1978).

Levery and Hakomori, *Methods in Enzymology vol. 138*, pp. 13–25, Academic Press (1987).

Akhrem, et al., "Structural Organization of the Carbohydrate Moiety of Human Transcortin as Determined By Methylation Analysis of the Whole Glycoprotein", *Biochimica et Biophysica Acta*, 714: 177–180 (1982).

Geyer, et al. "Capillary Gas Chromatography of Methyhexitol Acetates Obtained upon Methylation of N–Glycosidically Linked Glycoprotein Oligosaccharides", *Analytical Biochemistry*, 121: pp. 263–274 (1982).

Lowe and Nilsson, "A Method of Purification of Partially Methylated Alditol Acetates in the Mehtylation Analysis of Glycoproteins and Glycopeptides", *Analytical Biochemistry*, 136: 187–191 (1984).

Hakomori and Ishimoda, "A Rapid Permethylation of Glycolipid, and Polysaccharide Catalyzed by Methylsulfinyl Carbanion in Dimethyl Sulfoxide", *Journal of Biochemistry* 55: pp. 205–208 (1964).

Ciucanu and Kerek, "A Simple and Rapid Method for the Permethylation of Carbohydrates" *Carbohydrate Research* 131: 209–217 (1984).

Bjorndal, et al., "Gas–Liquid Chromatography and Mass Spectrometry in Methylation Analysis of Polysaccharides", *Angew. Chem. Internat. Edit.* 9: pp. 610–619 (1970).

*Handbook of Analytical Derivatization*, D. R. Knapp, John Wiley & Sons, Inc. pp. 543–545 (1979).

Peter Jackson, "The use of polyacrylamide–gel electrophoresis for the high–resolution separation of reducing saccharides labelled with the fluorophore 8–aminonaphthalene–1,3,6–trisulphonic acid", *Biochem. J.* 270: 705–713 (1990).

Peter Jackson, "Polyacrylamide Gel Electrophoresis of Reducing Saccharides Labeled with the Fluorophore 2–Aminoacridone: Subpicomolar Detection Using an Imaging System Based on a Cooled Charge–Coupled Device", *Analytical Biochemistry* 196: 238–244 (1991).

Suh and Waring, "Base Pairing between the 3' Exon and an Internal Guide Sequence Increase 3' Splice Site Specificity in the Tetrahymena Self–Splicing rRNA Intron", *Mol. and Cell. Biol.* 10: 2960–2965 (1990).

Winter, et al., "The Mechanism of Group I Self–splicing: An Internal Guide Sequence can be Provided in Trans", *EMBO Journal* 9: 1923–1928 (1990).

Doudna, et al., "RNA Structure, not Sequence, Determines the 5' Splice–Site Specificity of a Group I Intron", *Proc. Natl. Acad. Sci. USA* 86: 7402–7406 (1989).

*Primary Examiner*—Ralph Gitomer
*Attorney, Agent, or Firm*—Albert P. Halluin; J. David Smith; Howrey & Simon

[57] ABSTRACT

Methods and kits for structurally analyzing carbohydrate molecules are taught. Carbohydrates for analysis are derivatized (preferably methylated) and then hydrolyzed into constituent monosaccharides. The derivatized monosaccharides are then labeled by a fluorophore and separated from one another by electrophoresis. The identity of derivatized monosaccharides is established by comparison with identification standards. The electrophoresis separation patterns may be visualized by a charged coupled device camera or photographically.

19 Claims, 4 Drawing Sheets

FLUOROPHORE ASSISTED DERIVATIZATION ANALYSIS OF CARBOHYDRATES

This is a continuation-in-part of application Ser. No. 07/753,196 filed on Aug. 30, 1991 now abandoned.

FIELD OF THE INVENTION

The subject invention is in the field of chemical structural analysis, in particular the structural analysis of carbohydrates.

BACKGROUND OF THE INVENTION

Carbohydrates play a number of extremely important roles in the functioning of living organisms. In addition to their metabolic and storage roles, carbohydrates are covalently attached to numerous other molecules such as proteins and lipids. Molecules such as glycoproteins and glycolipids are generally referred to as glycoconjugates. The biological importance of the carbohydrate portion of glycoconjugates can be seen, for example, in the role the carbohydrate portions play in affecting the ability of glycoproteins to perform their biological functions, including such functions as ligand or receptor recognition.

Carbohydrates display an enormous amount of structural variation. This variation stems not only from the wide variety of available monosaccharide units that may be combined to form a larger polysaccharide or oligosaccharide, but from the multitude of possible structural linkages between monosaccharide units. For example, while an oligopeptide containing three different amino acids has six possible configurations, an oligosaccharide containing three different hexose monomers can form at least 200 possible structures. These molecules may vary enormously with respect to their biological properties. Thus it is of interest to provide methods for analyzing both the identity of the monosaccharides units in a given polysaccharide, and the structure of the linkages joining the monosaccharide units to one another.

A widely used method of analyzing the linkages between various monosaccharides sub-units of a complex carbohydrate is methylation analysis (often referred to as permethylation analysis) of the polysaccharide. Methylation analysis typically involves the methylation of the free hydroxyl groups on a polysaccharide. Since the hydroxyl groups participating in linkages between polysaccharides are not free for methylation, methylation of the polysaccharide reveals the nature of the linkages between monosaccharide units. After a polysaccharide has been methylated, the methylated polysaccharide is then hydrolyzed into its constituent monosaccharide units. The methylated carbohydrate monomers are then separated from each other by gas-liquid chromatography. The structure of the separated monosaccharide units is then identified by mass spectrometry.

Techniques for determining carbohydrate structures by methylation analysis are well established. See, for example, *Analysis of Carbohydrates by GLC and MS*, Chapter 9, editors Biermann and McGinnis, CRC Press (1988); Lindberg and Lonngren, *Methods in Enzyomology Vol.* 138, Academic Press (1978); Lavery and Hakomori, *Methods In Enzymology Vol.* 138, Academic Press (1987); Akhrem, et al., *Biochiamica et Biophysica Acta*, 714:177–180 (1982); Geyer, et al., *Analytical Biochemistry* 121:263–274 (1982); Lowe and Nilsson, *Analytical Biochemistry*, 136:187–191 (1984); Hakomori, *J. Biochem.*, 35:205 (1964); Ciucanu and Kerek, *Carbohydrate Research*, 151:209–217 (1984); Oakley, et al., *J. Carbohydrate Chemistry*, 4:53–65 (1985); Bjornadal, et al. *Angw. Chem. Int. Ed.*, 9:610 (1970); Neves, et al., *Carbohydrate Research*, 152:1–6 (1986).

Methylation analysis of carbohydrates has traditionally required large and expensive pieces of laboratory equipment, e.g., a mass spectrometer, and large quantities, e.g., several milligrams, of carbohydrate for analysis. Thus it is of interest to provide new methods of carbohydrates structural analysis employing comparatively low cost equipment and capable of providing useful data with considerably smaller sample sizes.

SUMMARY OF THE INVENTION

The subject invention provides for the determination of the chemical structure of a variety of carbohydrate molecules. The structure of carbohydrates of interest is determined by a process comprising derivatizing the free hydroxyl groups (or other functional sidegroups of the sample carbohydrate), hydrolyzing the derivatized carbohydrate into constituent monosaccharides, labeling the derivatized monosaccharide units with a fluorescent label, separating the labeled derivatized monosaccharides, identifying the structure of the labeled derivatized monosaccharides, preferably by comparison with derivatized monosaccharide standards. The preferred group for derivatization of the test carbohydrates is methyl. The separated derivatized monosaccharides are preferably visualized using an imaging system based on photoelectric detection means, such means including the use of laser-scanner photomultiplier tubes or charge coupled device (CCD) cameras. Information from the CCD camera may subsequently be stored in digital form and analyzed by various computer programs for comparing carbohydrate banding patterns between samples and identification standards.

Additionally, the gel separated derivatized carbohydrates may be transferred to an immobilizing membrane, i.e., blotted, and then probed with various carbohydrate-specific reagents whereby the structural identity of derivatized carbohydrates may be determined.

DESCRIPTION OF THE SPECIFIC EMBODIMENTS

The subject invention provides for the structural analysis of various carbohydrates by means of applying fluorophore assisted carbohydrate electrophoresis techniques to derivatized carbohydrates. Thus an important aspect of the subject invention is the separation of derivatized carbohydrates, especially derivatized carbohydrates differing with respect to each other only with regard to the sites of derivatization, by fluorophore assisted carbohydrate electrophoresis. Another aspect of the subject invention is to provide for the identification of the chemical structure of monosaccharide constituents of the carbohydrate for analysis. Of particular interest is the ability to distinguish between carbohydrate structures that differ with respect to each other as stereoisomers, enantiomers, or the site of derivatization. Hereinafter, the application of fluorophore assisted carbohydrate electrophoresis to derivatized carbohydrates will be referred to as fluorophore assisted derivatization analysis. As in traditional methylation analysis, i.e., methylation analysis involving mass spectrometry, structural information about the linkages between subunits, i.e., monosaccharides, in a carbohydrate may be obtained, at least in part, from the blockage of potential derivatization sites by the glycosidic linkage between subunits. Structural information may be gained because a carbohydrate has hydroxyl groups at various ring positions that are free for reaction with methylating (or similar derivatizing) agents; however, the ring sites involved in glycosidic linkages between rings are not available for methylation. After derivatization, the structure of the original carbohydrate may be established by determining which sites on the carbohydrate are modified by derivatization. For example, methylation of galactosylgalactose, i.e., D-Gal ($\alpha$1-4)-D-Gal, followed by hydrolysis yields two compounds 2,3,4,6-tetra-O-methyl-D-galactose and 2,3,6-tri-O-methyl-D-galactose; the 1 and the 4 positions on the two galactose subunits are unavailable for methylation because they are joined by the glycosidic linkage.

The general technique of fluorophore assisted derivatization analysis comprises several steps. First, the free hydroxyls (and other substituent groups available for bonding to other carbohydrates) on a carbohydrate sample of interest are completely derivatized. After the sample carbohydrate has been derivatized, the derivatized carbohydrate is hydrolyzed into its constituent monosaccharides. The mixture of derivatized monosaccharides is subsequently separated into its individual components by fluorophore assisted carbohydrate electrophoresis. The structure of each derivatized monosaccharide, including the site(s) of derivatization, may then be established by comparison with identification standards. The information about the derivatization sites may then be used to determine the linkage structures between individual monosaccharide units in the carbohydrate for analysis. The structural information about the linkages between monosaccharide units may be derived, at least in part, from the blockage of potential derivatization sites by a glycosidic linkage. Additional information about the structure of polysaccharides may be obtained by employing glycosidic enzymes of known specificity in conjunction with fluorophore assisted carbohydrate electrophoresis.

The term "derivatized carbohydrates" refers to carbohydrates having a derivatizing compound bonded to the free hydroxyls (and other substituent groups available for bonding to other carbohydrates) of the sample carbohydrate. The term "derivatized monosaccharides" refers to those derivatized carbohydrates that are monosaccharides. The term "derivatizing" refers to the process of producing a derivatized carbohydrate from a carbohydrate.

Carbohydrates for analysis by the method of the subject invention may be derivatized by a variety of derivatizing compounds. The available carbohydrate chemistry literature provides for numerous derivatizing compounds for carbohydrates and methods of derivatizing carbohydrates (for example see *Analytic Derivatization* by Knapp, John Wiley & Son, Inc. (1979)). In general, suitable derivatizing compounds contain a group that is capable of being covalently attached to carbohydrates for analysis at regions of the carbohydrate other than the glycosidic linkages joining monosaccharide units. Specific derivatizing compounds of interest are compounds that contain groups for bonding including: (1) functionalized hydrocarbyl compounds including (a) alkyl species, which may be substituted by a variety of functional groups such as hydroxyl, amino, halide, and the like, generally alkyl groups will have about 1 to 20 carbons, preferably 1 to 10 carbons, more preferably 1 to 5 carbons, and 1 carbon, i.e., iodomethane, being a particularly preferred functionalized hydrocarbyl compound; the alkyl derivatizing compounds may be branched or unbranched, (b) cycloalkyl species, such as cyclobutyl, cyclopentyl, and cyclohexyl, (c) aromatic species, substituted and unsubstituted such as benzyl, methybenzyl, carboxybenzyl, tosyl, pentaflouprophenyl, benzoyl, (2) heterocyclic species, such as morpholinic, piperdinyl, (3) carboxyl containing groups such as alkanoyl, ketal, acyl, acetal, (4) nitrogen containing species such as nitriles, azidos, and amides including, aldonitrile, phenylacetamidomethyl, benzhydroxylamine, methylbenzyhydroxylamine, cyanoethyl, phosphoramide, (5) silicon containing species such as silyls including, trimethylsily, dimethylsilyl, and (6) boron containing species such as boronates.

Also of interest for use as derivatizing compounds are blocking groups used for the in vitro synthesis of carbohydrates, including 9-fluorenylmethyloxycarbonyl, benzotriazolyl N-oxytri-dimethylamino-phoshonium hexafluorophosphate, dichloromethane, 2-(1H-benzotriazole-1-yl)-1,1,3,3-tetramethyluronium hexafluorophosphate, diisopropylcarbodiimide, dicyclohexylcarbodiimide, disopropylethylamine, N,N-dimethylformamide, 1-hydroxybenzotriazole, N-hydroxysuccinimide.

Additionally, groups used to convert carbohydrates to chromogenic substrate may also be of interest for use as derivatizing compounds. In general, derivatizing compounds of interest remain stably attached to the derivatized carbohydrate and do not significantly interfere with the fluorescent labeling of the reducing portion of the derivatized monosaccharide.

An advantage of the subject invention is that structural analysis of carbohydrates may be achieved using significantly smaller samples than required when performing methylation analysis in which the methylation products are analyzed in a mass spectrometer. This advantage is especially significant when the carbohydrate for analysis is rare. The quantity of sample carbohydrate for analysis need only be sufficient to be detectable as a fluorophore label. Generally, samples containing as little as one nanomole of the carbohydrate of interest may be employed.

The fluorophore assisted carbohydrate electrophoresis technique is described in detail in U.S. Pat. No. 4,874,492 and in U.S. patent application Ser. No. 07/317,480, filed Feb. 14, 1989, which are herein incorporated by reference. A brief description of this technique is provided as follows. Fluorophore assisted carbohydrate electrophoresis permits the electrophoretic separation of a complex mixture of carbohydrates into distinct bands on a gel or other separation medium. Prior to electrophoresis, a carbohydrate mixture for analysis is treated with a fluorophore label that combines with the reducing end of the carbohydrates for analysis. The fluorophore label permits the detection and quantitative measurement of the labeled carbohydrates by fluorescence. The fluorophore label either is charged or coupled with a charge imparting species when the fluorophore itself is uncharged. Thus the labelling process not only fluorescently tags the carbohydrates, but imparts an ionic charge, permitting hitherto uncharged carbohydrates to migrate in an electric field. Suitable fluorescent labels include 8-aminonapthalene-1,3,6-trisulphonic acid (ANTS), 1-amino-4-naphthalene sulfonic acid (ANSA), 1-amino-6,8-disulphonic acid (ANDA), lucifer yellow, 7-amino-1,3-naphthalene disulfonic acid, and 2-aminoacridone. A description of fluorophores suitable for use in the subject invention can be found in U.S. patent application No. 07/483,043 filed Feb. 16, 1990 and UK application GB/90/01448 filed Sep. 20, 1990 and published as PCT application WO 91/05256, which are herein incorporated by reference. After the carbohydrates have been labeled, the sample is subsequently subjected to polyacrylamide gel electrophoresis, or similar electrophoresis separation means, in order to separate and concentrate the labeled carbohydrates into bands.

Carbohydrates for analysis by fluorophore assisted derivatization analysis are preferably purified. The term "purified" as used herein preferably means 95% by weight, more preferably at least 99% by weight, of reducing carbohydrate molecules of the same type (but molecules not subject to labeling by the fluorophore label, including non-reducing carbohydrates, polypeptides, water, buffers and other small molecules, may be present). Purified carbohydrates for analysis by the subject invention may be prepared by fluorophore assisted carbohydrate electrophoresis.

The structure of carbohydrates may be determined by enzymatically cleaving carbohydrates of interest with glycosidases of known specificity, and separating the glycosidase digestion fragments so that the separated fragments can be analyzed by fluorophore assisted derivatization analysis. A preferred method of separating the digestion products is by fluorophore assisted carbohydrate electrophoresis. The fluorophore assisted carbohydrate electrophoresis separated fragments may then be eluted (elution may be by a variety of means commonly applied to polypeptide, e.g., electroelution, diffusion, dialysis, and the like), and subsequently analyzed by fluorophore assisted derivatization analysis. Thus the structure of a comparatively large polysaccharide may be determined by fragmenting the polysaccharide into smaller polysaccharide fragments by a process in which information is obtained about the nature of the linkage joining the fragments in the original molecule, and applying fluorophore assisted derivatization analysis to determine the structure of the individual fragments.

The technique of fluorophore assisted derivatization analysis requires that the derivatization of the carbohydrates for analysis proceed to an extent essentially the same as required for traditional methylation analysis. Thus, carbohydrates for analysis should be derivatized to a degree such that monosaccharides produced by hydrolyzing the derivatized carbohydrates for analysis containing underivatized hydroxyls (or other substituent groups available for bonding to other carbohydrates) are present in quantities insufficient to significantly interfere with the detection of maximally derivatized monosaccharide products of hydrolysis. The complete derivatization of the sample carbohydrates should be established prior to the hydrolysis of the sample carbohydrate. The extent to which the sample polysaccharide is derivatized may be determined by a variety of separation means capable of separating completely derivatized polysaccharides, from partially derivatized and non-derivatized carbohydrates. Suitable separation techniques include fluorophore assisted carbohydrate electrophoresis, capillary electrophoresis, high performance liquid chromatography, gas chromatography, paper chromatography, and thin layer chromatography.

Suitable methods of derivatizing carbohydrates of interest do not break the carbohydrate chain and do not interfere with the subsequent hydrolysis of the derivatized carbohydrate sample or the fluorescent labeling of the derivatized monosaccharide sub-units.

Additional structural information about carbohydrate samples for analysis may also be gained by derivatizing carbohydrates with derivatizing compounds that specifically react with distinct functional groups on the carbohydrate other than the primary hydroxyls on the carbon rings of the monosaccharides. Thus the presence of given functional groups (as well as the number present) on a carbohydrate for analysis may be determined after screening for differences in gel mobility by fluorophore assisted carbohydrate electrophoresis attributable to the derivatization process.

A significant advantage of the subject invention is that carbohydrates for analysis may be derivatized by a variety of derivatizing compounds other than compounds resulting in the addition of methyl groups, i.e., methylation. Traditional derivatization analysis of carbohydrate structure has required that the sample carbohydrates for structural analysis be methylated, as opposed to being derivatized by other derivatizing compounds that result in the covalent attachment of different substituents to the carbohydrate, because of the relative ease of analysis of the structure of the methylated monosaccharides (as opposed to other derivatized monosaccharides) by mass spectrometry.

A significant problem of methylating carbohydrates is that the methylation product of some methylated carbohydrates may be highly insoluble in aqueous (and other) solutions. By providing for the derivatization by derivatizing compounds that result in the attachment of groups other than methyl groups, the subject invention provides for the structural analysis of carbohydrates that are insoluble when methylated. Derivatizing carbohydrates with derivatizing compounds other than methyl donating compounds may give rise to derivatized carbohydrates that have significantly different solubility properties (in aqueous and other solvents) than their methylated counterparts. These altered solubility properties may be exploited to provide for the structural analysis of carbohydrates that have hitherto been difficult to analyze. For example, solubility in water may be increased by derivatization with an alkane substituted with a polar functional group.

After derivatization, the carbohydrate for analysis is hydrolyzed into constituent monosaccharide units. Hydrolysis may be achieved by any hydrolysis method that may be used in the traditional methylation analysis of carbohydrate structure. Hydrolysis is typically achieved by incubation of derivatized carbohydrates in an acidic solution, either dilute or concentrated, for a period of time sufficient to hydrolyze all of derivatized carbohydrate for analysis into its constituent monosaccharides other suitable methods of hydrolysis include incubation with enzymes having glycosidase activity. The literature on methylation analysis of carbohydrates provides details on how to perform hydrolysis by methods that are suitable for fluorophore assisted derivatization analysis, see, for example, Lindberg and Longren *Methods in Enzymology Volume* 50, pages 1–33, Academic Press (1978).

After the derivatized monosaccharides have been fluorescently labeled, the hydrolyzed sample is subsequently subjected to polyacrylamide gel electrophoresis, or similar electrophoresis separation means, in order to separate and concentrate the labeled carbohydrates into bands. The separated carbohydrates may be visualized directly by fluorescence under U.V. light, and the banding patterns stored photographically. Alternatively the separated carbohydrates may be visualized by photoelectric means, including laser-scanner photomultiplier tube systems and cooled charge coupled devices (CCD). CCDs are semiconductor imaging devices that permit the sensitive detection of emitted light. CCDs and their uses are described in U.S. Pat. Nos. 4,874,492 and 4,852,137 which are herein incorporated by reference. The image produced by the CCD may be subsequently transferred to a computer wherein the bands may be analyzed with respect to intensity, mobility, standards, and the like.

In a preferred embodiment of the subject invention, carbohydrate band data from the gels used to separate and quantitate bands of derivatized monosaccharides are read by means at a CCD and stored in a computer usable form. The image detected by the CCD, or other detection system, may be analyzed by image analysis software such as Optimas™ (Bioscan™) or similar image analysis programs. The data may be subjected to analysis by a variety of image analysis software programs. Image analysis Software programs of interest include those with the ability to quantitate band intensity, measure band mobility, determine the relative molecular weight of carbohydrates forming bands, compare the standards with the samples for analysis, remove unwanted background information, and perform various forms of statistical analysis. In a preferred embodiment of the subject invention, quantitative data obtained from the fluorophore assisted carbohydrate electrophoresis is manipulated and/or presented in electronic spreadsheet form, e.g., Lotus 1-2-3™, Microsoft Excel™.

When performing fluorophore assisted derivatization analysis, electrophoretic separation should take place to an extent sufficient to resolve the bands of derivatized monosaccharides. Electrophoresis may be in one or in two dimensions. Two-dimensional separation of carbohydrates by fluorophore assisted carbohydrate electrophoresis is described in U.S. Pat. No. 4,975,165, which is herein incorporated by reference.

While the techniques used to separate the derivatized carbohydrates are essentially those described in U.S. Pat. No. 4,874,492, these electrophoresis separation techniques are preferably adjusted so as to optimize for separation of derivatized carbohydrate monosaccharide units. These optimizations include the use of relatively high concentrations, i.e., 20%–40% polyacrylamide and the use of relatively high concentrations of bis-acrylamide cross-linker, i.e., 1–5%. The SDS-PAGE buffer and other reagents are preferably compatible with the use of micellar electrophoresis. The carbohydrates derivatized with "polar" or "hydrophilic" reagents can be separated using conventional polyacrylamide gel methods described in U.S. Pat. No. 4,874,492 and in U.S. patent application Ser. No. 07/317,480, filed Feb. 14, 1989 which are incorporated by reference.

Carbohydrates derivatized using "hydrophobic" or conventional organic chemistry derivatization reagents can be separated in polyacrylamide gels by adding ionic detergents such as SDS, non-ionic detergents such as NP-40, Triton X-100 or bile acids, or by incorporating in to the gel matrix various alcohols for example methoxyethanol or ethanol, alkanes, or dimethylformamide. Finally for the hydrophobic derivatives one can chemically derivatize the polyacrylamide using alkanes or other agents to make it compatible with the derivatized carbohydrates.

In a preferred embodiment of the subject invention, identification standards are included on gels used to separate derivatized monosaccharides in the samples for analysis; however, the information embodied by the identification standards, e.g., band migration distance and band intensity, may also be obtained by comparison with stored records made from identification standards previously subjected to the fluorophore assisted carbohydrate electrophoresis under conditions similar to the conditions the samples for analysis were exposed to.

Identification standards may be monosaccharides derivatized at 0, 1, 2, or more hydroxyl groups (or other substituent groups available for bonding to other carbohydrates) on the carbon ring of a monosaccharide. Identification standards may contain one or more monosaccharides. Identification standards may contain one or more derivatized monosaccharides that differ with respect to each other only by virtue of the sites of derivatization. In addition to differing with respect the site(s) of derivatization, identification standard monosaccharides may also differ with respect to each other by virtue of numerous other structural differences, including the number of carbon atoms in the ring, the location of the anomeric oxygen, stereoisometrically, etc. Preferred identification standards include mixtures of individual derivatized monosaccharides present in equimolar amounts, and derivatized by the same derivatizing compound. Identification standards are fluorescently labeled, and are preferably fluorescently labeled by the same fluorescent tagging reagent as the samples for identification. Identification standard carbohydrates derivatized at specific sites may be obtained from commercial sources or may be produced by derivatizing carbohydrates with known structures and subjecting them to hydrolysis.

Identification standards may be labeled prior to the labeling of the samples for analysis; however, identification standards are preferably labeled concomitantly with the labeling of the carbohydrates for analysis (but not in the same reaction vessel as the carbohydrates for analysis). Furthermore, the monosaccharides in the identification standards are preferably quantitated so as to provide for quantitative and/or qualitative comparisons with the derivatized monosaccharides produced by the hydrolysis of the derivatized samples for analysis.

Individual derivatized monosaccharides may also be identified by blot analysis. After derivatized monosaccharides are separated by fluorophore electrophoresis, the separated monomers may be transferred in situ from the gel and immobilized onto a membrane by blotting as described in U.S. Pat. No. 5,019,231, which is herein incorporated by reference. The membrane containing the immobilized derivatized carbohydrates may then be exposed to labeled reagents, such as antibodies and the like, capable of specifically binding with monosaccharides suspected of being present on the membrane. The binding specificity of these binding reagents may be dependent or not dependent on the derivatization pattern of the monosaccharide for which the reagent is specific.

The subject invention also includes kits for performing fluorophore assisted derivatization analysis of carbohydrates. Fluorophore assisted derivatization analysis kits provide collections of reagents required for performing the above-described technique of fluorophore assisted derivatization analysis. Suitable kits enable laboratories to conveniently perform the procedure. Kits may include identification standards, fluorescent label, blotting and binding materials, e.g., membranes, carbohydrate specific binding reagents, instructions, sample containers, derivatizing compounds (e.g., alkylating agents), glycosolytic enzymes, hydrolytic acids or other hydrolytic chemicals and polyacrylamide gel reagents. More complete kits may include equipment for performing fluorophore assisted carbohydrate electrophoresis, such as polyacrylamide gel apparatus, CCDs, computers, software, and the like. Reagents included in fluorophore assisted carbohydrate electrophoresis diagnosis kits are preferably provided in premeasured amounts. The kits may also include the instructions for carrying out the fluorophore assisted carbohydrate electrophoresis method of the present invention.

The invention having been described, the following examples are offered to by way of illustration of the invention, not by way of limitation.

EXAMPLES

Experiment 1

Performing Permethylation and Hydrolysis

Materials

Redistilled DMSO; Powdered NaOH, Methyl Iodine (Iodomethane), $CHCl_3$.

Method:

(4–5 mg) Sample material was desiccated to dryness and then dissolved in 0.5 ml redistilled DMSO. 20 mg powdered NaOH and 0.1 ml of iodomethane were subsequently added. The mixture was then stirred at 100 RPM under a dry nitrogen atmosphere for 6 min at 25° C. 2 ml each of water and $CHCl_3$ were added and the methylated product was partitioned into the $CHCl_3$ phase. The $CHCl_3$ phase was washed with 5–10 ml water three times. 20 mg of dry sodium sulfate ($Na_2SO_4$) was added to the $CHCl_3$ to remove residual traces of water.

The methylated sample was then hydrolyzed by incubation in 2 molar trifluoroacetic acid for 4 hours according to the method of Ciucanu and Kerek. *Carbohydrate Research*, 131:209–217 (1984).

Fluorescent Labelling and Separation

Approximately 1 nanomole of purified methylated and hydrolyzed carbohydrate sample was placed in a microcentrifuge tube and dried using a centrifugal vacuum evaporator (c.v.e.). To each dried sample was added 5 $\mu$l of 0.2 m 8-aminonapthalene-1, 3, 6-trisulphonic acid solution in acetic acid/water (3:17 v/v) and 5 $\mu$l of 1.0M $NaCNBH_3$ solution in dimethyl sulphoxide (DMSO). The solution was mixed, by vortexing briefly centrifuged at 10,000 g to ensure that all the reactants are in the tips of the tubes, and then incubated at 37° C. for 15 hours. The reaction mixture was dried under vacuum for 4 hours in a c.v.e. at approximately 45° C. and dissolved in a suitable concentration of electrophoresis sample buffer, so that the concentration of each labeled saccharide was 100 pmol/$\mu$.

The labeled samples were subjected to SDS polyacrylamide gel electrophoresis using a standard type electrophoresis apparatus, such as that from Hoefer Scientific Instruments. The electrophoresis buffer used is based on the Tris/HCL/glycine discontinuous system of Laemmli, with 10% SDS throughout. The polyacrylamide gel consists of 35% (w/v) acrylamide containing 1% (w/v) NN', methylenebisacrylamide respectively as a cross linker. The polymerization of the gel was initiated by the addition of 20 $\mu$l 10% (w/v) ammonium persulphate solution and 10 $\mu$l of N,N,N',N'-tetramethyl-ethylenediamine/12 ml of gel solution. The resolving gel size is 100 mm high×120 mm wide×approx. 0.3 mm thick. A stacking gel is used. The sample wells are 7 mm wide. Samples are electrophoresed at 2000 V for 240 minutes until the buffer front reaches approximately 5–10 mm from the gel base. All voltages are held constant. The gels are cooled to 5–7° C. by the surrounding stirred lower electrode buffer.

The gel was photographed using a cooled CCD camera system, i.e., an Astromed CCD camera, see, U.S. Pat. No. 4,874,492, herein incorporated by reference. The gel was also photographed under U.V. illumination, i.e., a light box with a maximum emission wavelength of 302 nm and a power of approximately 700 uW/$cm^2$. A Polaroid type 55 film (ISO 50), which gives both a negative and a positive photograph, a Wratten 8 gelatin filter (Kodak), an aperture of f4.5 and an exposure time of 50 seconds were used to record the gel pattern.

Methylation Analysis

Maltose, maltotriose, man-alpha-1-3 mannose, and galactose-beta-1-4-N-acetylglucosamine were permethylated using NaOH-methyl iodine, as described above, and verified as being completely derivatized by TLC. TLC was performed using Merck® HPTLC plates and a benzene:acetone (1:1 vol/vol) separating solution. The separated carbohydrates were detected by spraying the plates with a 0.2% orcinol solution. The sprayed plates were subsequently heated to 150° for 10 minutes and the locations of the purple spots were noted. Samples were then hydrolyzed in 2 molar trifluoroacetic acid for 20, 60, 90 and 120 minutes. The resulting methylation products were then dried down in a vacuum concentrator and subjected to fluorophore labeling and electrophoresis.

The carbohydrate banding patterns produced by electrophoresis could be distinguished from one another. Similar results are obtainable by replacing NaOH-methyl iodine with NaOH-ethyl, propyl, butyl iodide and other similar carbohydrate derivatizing compounds as described herein and known in the art.

EXAMPLE II

Electrophoresis of Derivatized Oligosaccharides

Reagents: Dimethylsulfoxide (DMSO) was analytical-grade solvent dried over molecular sieves Type 3A. Methyl iodide, ethyl iodide, pentyl iodide, and iodoacetamide were 99+% grade from Aldrich. Chloroform, methanol, dichloromethane, acetone and dioxane were HPLC grade solvents. Baker Analyzed, aldehyde free glacial acetic acid and HPLC/Spectro grade trifluoroacetic acid were used. The fluorophores 8-amino-1,3,5-naphthalenetrisulfonic acid, disodium salt (ANTS) and 7-amino-1,3-naphthalenedisulfonic acid, monopotassium salt (ANDA) were purchased from TCI America, Inc. and Aldrich, respectively, and recrystallized in water/ethanol. The fluorophore 2-aminoacridone (AMAC) was purchased from Molecular Probes, Inc. The monosaccharides, disaccharides, and oligosaccharides were purchased from Sigma, Pierce and Dionex.

Instrumentation: Fluorophore assisted carbohydrate electrophoresis (FACE) was performed using apparatus produced by Glyko was used to run the gels and image the gels.

Derivatization: The methylation of the carbohydrates was performed essentially as described in Ciucanu and Kerek, *Carbohydrate Research* 131:209–217 (1984). Most of the methylated products were detected by running thin layer chromatography (tlc) in benzene/acetone (1:1) solvents and by spraying with 0.2% orcinol in 10% sulfuric acid and heated for 10 minutes with a heat gun. To assure complete methylation, D-glucose, 3-fucosyllactose and stachyose were remethylated by the same procedure and the same spots were observed in the tlc. Methylated D-glucose, D-galactose, D-mannose and maltose were purified by column chromatography with silica gel 200–425 mesh type 60A (20 parts silica gel to 1 part sample) and eluted with dichloromethane and mixtures of dichloromethane/acetone with increasing concentrations of acetone to 5%. See Table I for the mono-, di-, oligosaccharides methylated. The other methylated products were not purified prior to the hydrolysis step. The procedures for producing ethylated, pentylated, etc., carbohydrates was essentially the same as the procedure used to produce methylated carbohydrates, except that the iodide compound used for the reaction was changed so as to obtain the desired derivatization product.

PAGE: Polyacrylamide gels were prepared according to standard procedures. The gels were loaded with 1–2 μl of samples (ideally 50 picomoles) and run in a Glyko gel box with 0.05 M tris/0.05M tris-tricine buffer pH 8.1 for about 1½ hours at a constant current of 15 ma per gel and not exceeding 1000 volts until the orange loading dye (thorin 1) was ½ the distance down the plate. Gels were also run at a constant voltage of 1000 volts for about 6 hours or until the fluorophore band was about 2 cm from the bottom of the glass plate. The fluorescent gel bands were imaged by a CCD.

TABLE I

ANTS LABELED HYDROLYZED PERMETHYLATED SACCHARIDES

| No. | Abbreviated formula | Trivial Name | Hydrolyzed, Methylated Derivatives |
|---|---|---|---|
| 1. | L-Fuc | fucose | 2,3,4-tri-O-methyl-L-fucose |
| 2. | D-Gal | galactose | 2,3,4,6-tetra-O-methyl-D-galactose |
| 3. | D-Glc | glucose | 2,3,4,6-tetra-O-methyl-D-glucose |
| 4. | D-Man | mannose | 2,3,4,6-tetra-O-methyl-D-mannose |
| 5. | | | 3-O-methyl-D-glucose |
| 6. | D-Fru | fructose | 1,3,4,6-tetra-O-methyl-D-fructose |
| 7. | D-Gal($\alpha$1-4)-D-Gal | galactosylgalactose | 2,3,4,6-tetra-O-methyl-D-glactose<br>2,3,6-tri-O-methyl-D-galactose |
| 8. | D-Gal($\alpha$1-6)-D-Gal | swietenose | 2,3,4,6-tetra-O-methyl-D-alactose<br>2,3,4-tri-O-methyl-D-galactose |
| 9. | D-Glc($\alpha$1-4)-D-Glc | maltose | 2,3,4,6-tetra-O-methyl-D-glucose<br>2,3,6-tri-O-methyl-D-glucose |
| 10. | D-Glc($\alpha$1-6)-D-Glc | isomaltose | 2,3,4,6-tetra-O-methyl-D-glucose<br>2,3,4-tri-O-methyl-D-glucose |
| 11. | D-Man($\alpha$1-2)-D-Man-$\alpha$-OMe | | 2,3,4,6-tetra-O-methyl-D-mannose<br>3,4,6-tri-O-methyl-D-mannose |
| 12. | D-Man($\alpha$1-3)-D-Man | | 2,3,4,6-tetra-O-methyl-D-mannose<br>2,4,6-tri-O-methyl-D-mannose |
| 13. | D-Gal($\beta$1-3)-D-GlcNAc-$\beta$-OMe | | 2,3,4,6-tetra-O-methyl-D-galactose<br>N-methyl-2-acetamido-2-deoxy-4,6-di-O-methyl-O-glucose |
| 14. | D-Gal($\beta$1-4)-D-GlcNAc | N-acetyllactosamine | 2,3,4,6-tetra-O-methyl-D-galactose<br>N-methyl-2-acetamido-2-deoxy-3,6-di-O-methyl-D-glucose |
| 15. | D-GalNAc($\beta$1-3)-D-Gal-$\alpha$-OMe | | 2,416-tri-O-methyl-D-galactose |
| 16. | D-GlcNAc($\beta$1-3)-D-Gal-$\beta$-OMe | | 2,4,6-tri-O-methyl-D-galactose |
| 17. | L-Fuc($\alpha$1-2)-D-Gal($\beta$1-4)-D-Glc | 2'fucosyllactose | 2,3,4-tri-O-methyl-L-fucose<br>2,3,6-tri-O-methyl-D-glucose<br>3,4,6-tri-O-methyl-D-galactose |
| 18. | L-Fuc($\alpha$1-3)-[D-Gal($\beta$1-4)]-D-Glc | 3-fucosyllactose | 2,3,4,Ari-O-methyl-L-fucose<br>2,3,4,6-tetra-O-methyl-D-galactose<br>2,6-di-O-methyl-O-glucose |
| 19. | D-Man($\alpha$1-6)[D-Man($\alpha$1-3)]D-Man-$\alpha$-OMe | | 2,3,4,6-tetra-O-methyl-D-mannose<br>2,4-di-O-methyl-O-mannose |
| 20. | D-Gal($\alpha$1-6)-D-Gal($\alpha$1-4)-D-Glu($\alpha$1-2)-D-Fru | stachyose | 1,3,4,6-tetra-O-methyl-D-fructose<br>2,3,6-tri-O-methyl-D-glucose<br>2,3,4,6-tetra-O-methyl-D-galactose<br>2,3,4-tri-O-methyl-D-galactose |

Hydrolysis and Fluorophore Labeling: The methylated mono-, di-, polysaccharides (1–3 μg) were hydrolyzed in 100 μl of 100% glacial acetic acid and 100 μl of 4 N trifluoroacetic acid (1:1) in a 0.5 ml microfuge tube at 80° C. overnight. The solvent was evaporated under a stream of nitrogen, 10 μl of water added and evaporated to make sure all acids were gone. The monosaccharide hydrolysate were dissolved in 500 ul dioxane and the di-, tri-, polysaccharides in chloroform/methanol (2:1). Aliquots (10 μl) were taken, blown dry with nitrogen, and 10 μl each of 0.15 M Fluorophore (ANTS, ANDA, AMAC) and 10 μl of 1 M NaCNBH$_3$ added. The labeling reaction was incubated at 37° C. overnight, speed vacuum dried, and dissolved in 100–200 μl loading solution (12.5% glycerol in water).

RESULTS

The positions of the standards were established by comparison to the more mobile bands of Test Mixture 5 (TM5) described in Jackson, *J. Biochem.* (Great Britain) 270:705–713 (1990). TM5 is: 6-deoxyglucose, glucose, galactose, N-acetyl-galactosamine, galactosylgalactose, lactose, maltose, galactobiose, cellotriose, maltotriose, maltotetraose, maltopentaose, maltohexaose, and maltoheptaose. The standards were prepared from fluorophore labeled, hydrolyzed, methylated, monosaccharides, disaccharides, and trisaccharides. Tlc (thin layer chromatography) performed on the hydrolyzed tetramethylated-D-glucose matched the tlc results obtained for 2,3,4,6-tetra-O-methyl-D-glucose purchased from Sigma, thus indicating that complete methylation was obtained.

Figure 1:
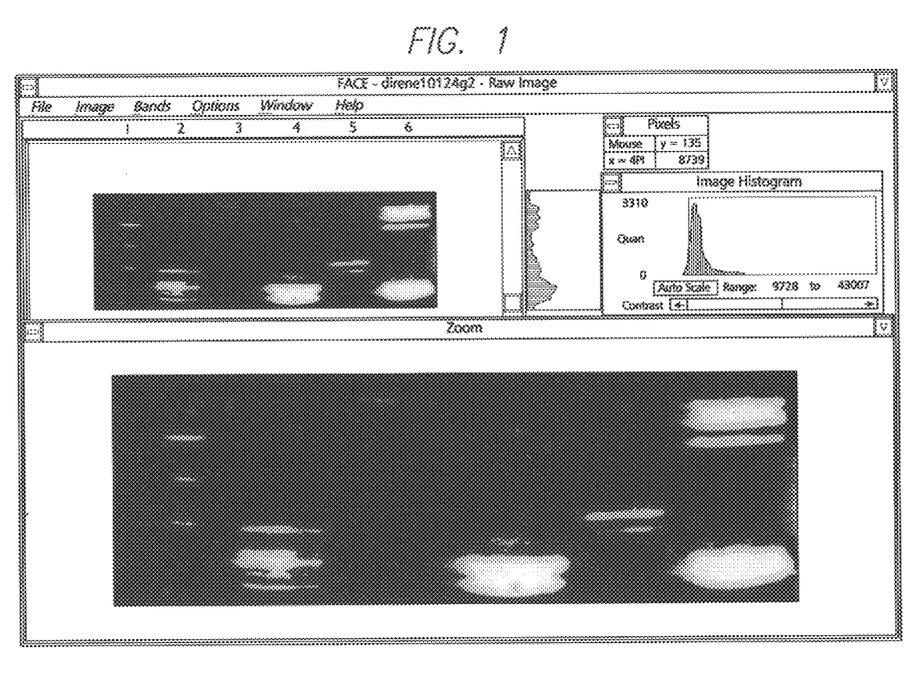
FIG. 1 is a photograph of a computer screen output of a CCD image of methylated monosaccharides labeled with different fluorophore separated by FACE (fluorophore assisted carbohydrate electrophoresis).

FIG. 1 shows the relative gel migration positions found for the fluorophore labeled fully derivatized monosaccharides (note: all but the pyranose ring oxygen is not methylated). ANTS labeled tetramethylated D-glucose migrates the fastest, followed by ANTS labeled trimethylated L-fucose, tetramethylated D-galactose, and tetramethylated D-mannose.

The ANTS labeled fully ethylated monosaccharides of fucose, galactose, glucose and mannose did not separate into four bands (3 bands were observed); however, a slight modification in gel composition revealed 4 bands. Experiments attempting to separate the four ANDA labeled fully methylated derivatives of glucose, fucose, galactose and mannose revealed 3 bands.

Figure 2:
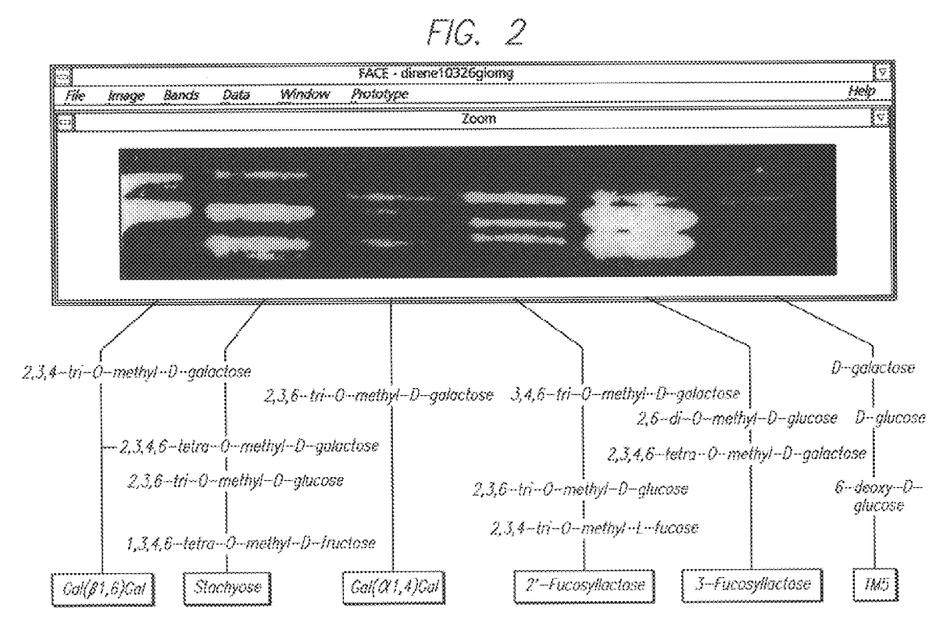
FIG. 2 is a photograph of a computer screen output of a CCD image of ANTS labeled, hydrolyzed, methylated saccharides separated by FACE.

Labeled partially methylated monosaccharides (linkage positions contain hydrogen instead of methyl groups) were obtained from the reducing end of the hydrolyzed permethylated disaccharides. The identity of the fully methylated monosaccharide from the non-reducing end of the disaccharide was confirmed by comparison previously established standards. Trisubstituted, i.e., 3 methyl groups, derivatives of monosaccharides can be distinguished from each other by fluorophore assisted carbohydrate electrophoresis. For example, ANTS labeled 2,3,6-tri-O-methyl-D-galactose migrates faster than that of 2,3,4-tri-O-methyl-D-galactose (FIG. 2).

Figure 3:
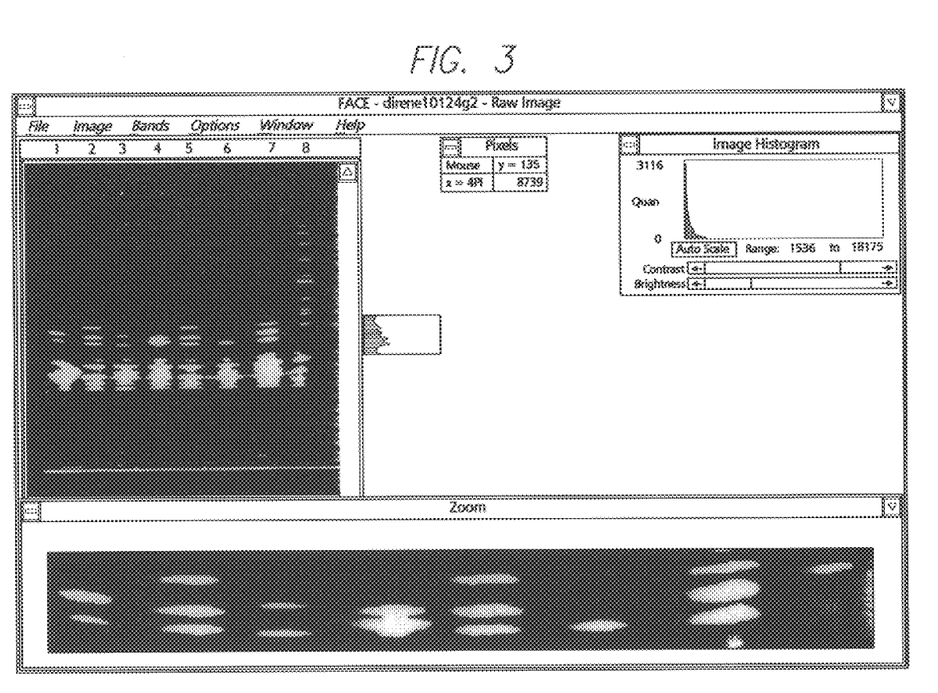
FIG. 3 is a photograph of a computer screen output of a CCD image of ANTS labeled, hydrolyzed, methylated saccharides separated by FACE.

The glycosidic linkage positions of 3-fucosyllactose and 2'-fucosyllactose were verified by fluorophore assisted carbohydrate electrophoresis performed on the hydrolysis product of the fully methylated, i.e., fully derivatized, compounds. In the case of 3-fucosyllactose, the trimethylated fucose is clearly observed, with the tetramethylated galactose and trimethylated glucose band overlapping. A minor change in gel composition resulted in the separation of 2 overlapping bands of the ANTS-labeled 3-fucosyllactose hydrolysis seen in a first attempt at PAGE separation into three distinct bands (FIG. 3). Comparable experiments performed with ANTS-labeled, methylated 2'-fucosyllactose hydrolysis product resulted in the formation of three distinct bands that matched the band positions of the standards. The 3-fucosyllactose image also displayed a weak band from a 2'-fucosyllactose contaminant.

Figure 4:
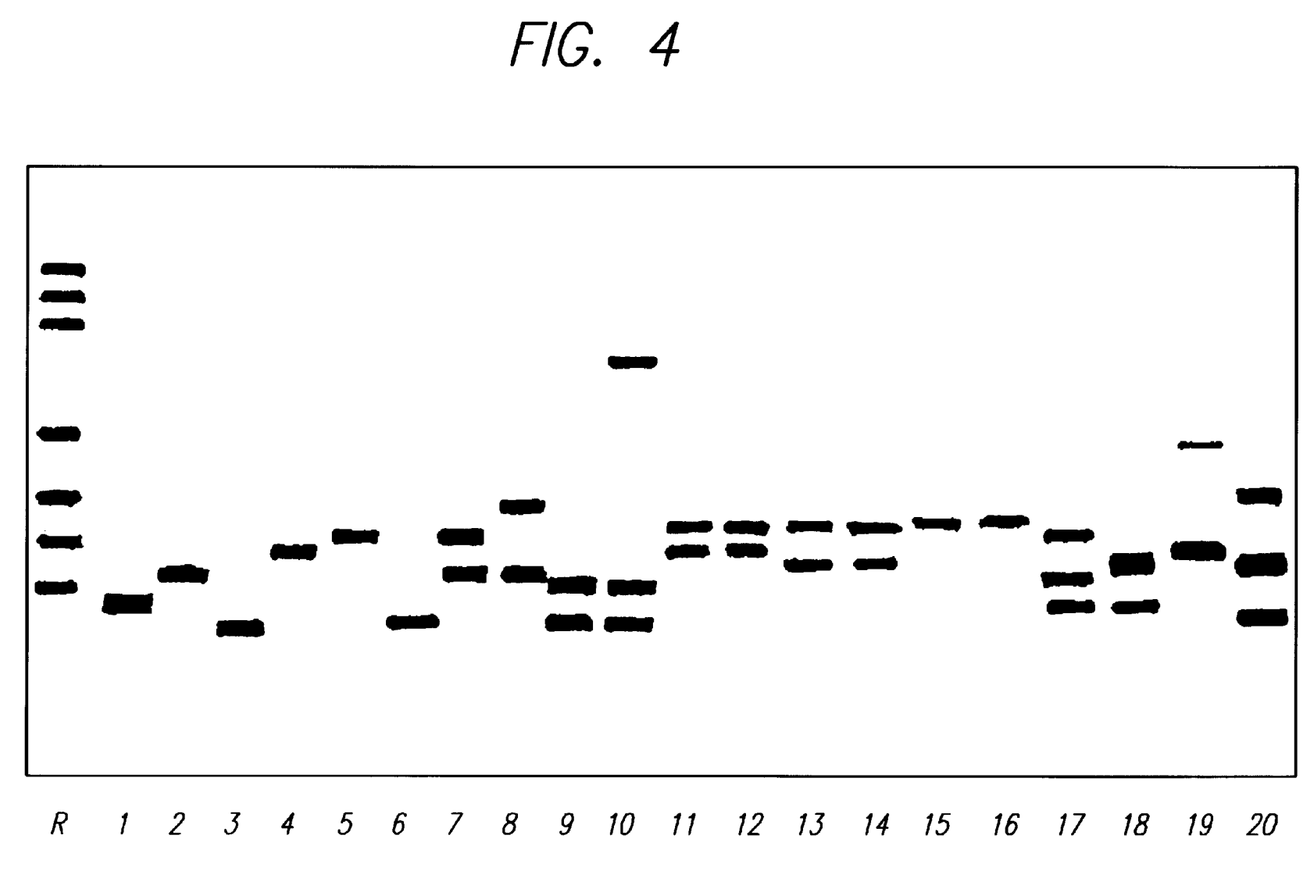
FIG. 4 is a schematic diagram of the FACE separation of the ANTS-labeled hydrolysis production of methylated saccharides of Table 1. The lines are labeled according to Table 1.

Table 1 lists all the saccharides subjected to fluorophore assisted carbohydrate electrophoresis by methylation and ANTS labeling. Line 5, 3-O-methyl-D-glucose, was a commercially obtained methylated standard. FIG. 4 is a schematic diagram of the fluorescent banding patterns obtained by fluorophore assisted carbohydrate electrophoresis of the products of methylating, hydrolysing, and ANTS-labeling the carbohydrates of Table 1. The line numbering in FIG. 6 corresponds to the numbering in Table 1. The order of the compounds in the column of Table 1 entitled "Hydrolyzed, Methylated, Derivatives" are listed in order of decreasing gel mobility.

The experiments performed confirm almost all of the expected band positions (exception N-acetylneuraminic acid) for ANTS labeled methylated monosaccharide derivatives from the hydrolysis of a glycoprotein standard GPO3, obtained from Dionex, can be resolved by electrophoresis.

EQUIVALENTS

The foregoing written specification is considered to be sufficient to enable one skilled in the art to practice the invention. Indeed, various modifications of the above-described modes for carrying out the invention which are obvious to those skilled in the field of organic chemistry or related fields are intended to be within the scope of the following claims.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

That whichis claimed:

1. A method of analyzing structural relationships between monosaccharides of a carbohydrate comprising:

a) derivatizing a carbohydrate with a carbohydrate derivatizing agent which covalently binds to the free functional groups of the carbohydrate to form a derivatized carbohydrate;

b) converting said derivatized carbohydrate into derivatized monosaccharides by breaking the glycosidic bonds of said derivatized carbohydrate;

c) forming labeled derivatized monosaccharides by reacting said derivatized monosaccharides with a fluorescence labelling compound;

d) separating said labeled derivatized monosaccharides by electrophoresis; and e) identifying said labeled derivatized monosaccharides by comparing the electrophoresis mobility of said labeled derivatized monosaccharides to a monosaccharide standard, said monosaccharide standard comprising monosaccharides derivatized with said carbohydrate derivatizing agent and labelled with said fluorescence labelling compound.

2. A method according to claim 1 wherein said carbohydrate derivatizing agent covalently binds a substituent to the carbohydrate functional group wherein said substituent is selected from the group consisting of a heterocycle, cycloalkyl, carboxyl, alkyl, substituted alkyl, an aryl, an alkanoyl, ketal, acetal and acyl.

3. A method according to claim 2 wherein said substituent is selected from the group consisting of cyclobutyl, cyclopentyl, and cyclohexyl.

4. A method according to claim 2 wherein said substituent is selected from the group consisting of benzyl, methylbenzyl, carboxybenzyl, tosyl, pentafluoroprophenyl and benzoyl.

5. A method according to claim 2 wherein said substituent is selected from the group consisting of morpholinic and piperdinyl.

6. A method according to claim 1 wherein said carbohydrate derivatizing agent is selected from the group consisting of nitriles, azidos and amides.

7. A method according to claim 6 wherein said carbohydrate derivatizing agent is selected from the group consisting of aldonitrile, phenylacetamidomethyl, benzhydroxylamine, methylbenzyhydroxylamine, cyanoethyl and phosphoramide.

8. A method according to claim 1 wherein said carbohydrate derivatizing agent is selected from the group consisting of trimethylsilyl, dimethylsilyl and boronates.

9. A method according to claim 1 wherein said carbohydrate derivatizing agent is selected from the group consisting of 9-fluorenylmethyloxycarbonyl, benzotriazolyl N-oxytridimethylamino-phoshonium hexafluorophosphate, dichloromethane, 2-(1H-benzotriazole-1-yl)-1,1,3,3-tetramethyluronium hexafluorophosphate, diisopropylcarbodiimide, dicyclohexylcarbodiimide, disopropylethylamine, N,N-dimethylformamide, 1-hydroxybenzotriazole, N-hydroxysuccinimide.

10. A method according to claim 1 wherein said carbohydrate derivatizing agent converts said carbohydrate to a chromogenic substrate.

11. A method according to claim 1, wherein said derivatizing agent is a methylating agent.

12. A method according to claim 1, wherein said derivatized monosaccharide is labeled with a fluorophore selected from the group consisting of 8-aminonapthalene-1, 3, 6-trisulphonic acid, 1-amino-6, 8-disulphonic acid, lucifer yellow and 2-aminoacridone.

13. A method according to claim 1, said method further comprising the step of visualizing said labeled derivatized monosaccharides by means of a charge-coupled device.

14. A method according to claim 1, wherein said electrophoresis is 2-dimensional.

15. A method according to claim 1, wherein said electrophoresis step employs an electrophoresis separation gel, said method further comprising the steps of
   a) transferring said labeled derivatized monosaccharides in situ from said gel to an immobilizing membrane, and
   b) incubating said membrane with a solution comprising a carbohydrate specific binding reagent.

16. A method of analyzing the structural relationships between monosaccharides of a carbohydrate comprising:
   a) digesting a carbohydrate with a glycosidase, whereby digestion fragments are produced,
   b) purifying said digestion fragments by fluorophore assisted carbohydrate electrophoresis; and
   c) applying the method of claim 1 to the purified digestion fragments.

17. A kit for performing monosaccharide linkage structural analysis of carbohydrates, said kit comprising, a carbohydrate derivatizing agent which covalently binds to free functional groups of the carbohydrates to form derivatized corbohydrates, a glycosidic bond hydrolyzing agent and a fluorophore label.

18. A kit according to claim 17 said kit further comprising a monosaccharide standard, said monosaccharide standard comprising monosaccharides derivatized with a carbohydrate derivatizing agent and labelled with a fluorescence labelling compound.

19. A kit according to claim 18 said kit further comprising a charge-coupled device detection system and image analysis software.

* * * * *